US009428620B2

(12) United States Patent
Williams et al.

(10) Patent No.: US 9,428,620 B2
(45) Date of Patent: Aug. 30, 2016

(54) MICROBIAL GROWTH ENHANCEMENT FROM A DRY FILM ADDITIVE

(71) Applicant: U.S. Army Research Laboratory ATTN: RERL-LOC-I, Adelphi, MD (US)

(72) Inventors: Andre A. Williams, Havre de Grace, MD (US); Joshua A. Orlicki, Havre de Grace, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 14/589,047

(22) Filed: Jan. 5, 2015

(65) Prior Publication Data

US 2015/0126689 A1 May 7, 2015

Related U.S. Application Data

(62) Division of application No. 13/926,097, filed on Jun. 25, 2013, now Pat. No. 9,040,640.

(51) Int. Cl.

| | |
|---|---|
| ***C08G 83/00*** | (2006.01) |
| ***C12N 1/20*** | (2006.01) |
| ***C12N 1/16*** | (2006.01) |
| ***C08G 63/91*** | (2006.01) |

(52) U.S. Cl.

CPC ........... *C08G 83/005* (2013.01); *C08G 63/912* (2013.01); *C12N 1/16* (2013.01); *C12N 1/20* (2013.01)

(58) Field of Classification Search

CPC .... C08G 63/912; C08G 83/005; C12N 1/16; C12N 1/20

See application file for complete search history.

(56) References Cited

PUBLICATIONS

Jena, K.K., et al.; Journal of Physical Chemistry, 2007, p. 8801-8811.*

* cited by examiner

*Primary Examiner* — Robert Jones, Jr.

(74) *Attorney, Agent, or Firm* — Robert Thompson

(57) ABSTRACT

A hyperbranched polymer based on one or more repeating units of an $AB_x$ type monomer, wherein A and B are functional groups and x is greater than or equal to 2, wherein A reacts with, or substantially reacts with, B, wherein B is fractionally functionlized with a plurality of functional groups comprising a first functional group comprising a $C_6$-$C_{30}$ alkyl chain attached to the repeating unit through a carbonyl group (C═O) via an ester linkage, a second functional group comprising a partially fluorinated or perfluorinated $C_3$-$C_{20}$ alkyl chain attached to the repeating unit through a carbonyl group (C═O) via an ester linkage, and a third functional group comprising substantially one of a stabilized radical source attached to the repeating unit via a $C_0$-$C_6$ tether, or a 5 to 8 member chloroamide heterocycle of carbon and nitrogen that is attached to the repeating unit via a $C_2$-$C_6$ tether.

6 Claims, 2 Drawing Sheets

MICROBIAL GROWTH ENHANCEMENT FROM A DRY FILM ADDITIVE

BACKGROUND

This application is a divisional of co-pending application Ser. No. 13/926,097 filed in the name of A. Williams and J. Orlicki on Jun. 25, 2013. The complete disclosure of which, in its entirety, is herein incorporated by reference.

GOVERNMENT INTEREST

Governmental Interest—The invention described herein may be manufactured, used and licensed by or for the U.S. Government.

FIELD OF USE

Embodiments of the present invention generally relate to additives that promote the growth of microorganisms.

BACKGROUND

As the realm of genetically modified microorganisms increases, the potential applications for promoting microbial growth similarly increase. A large array of important products may soon be produced through microbial means.

Therefore, the inventors have provided improved additives that promote the growth of microorganisms.

SUMMARY

At least some embodiments of the present invention relate to a hyperbranched polymer based on one or more repeating units of an $AB_x$ type monomer, wherein A and B are functional groups and x is greater than or equal to 2, and wherein the A functional group reacts with, or substantially reacts with, the B functional group, and wherein B is fractionally functionlized with a plurality of functional groups, wherein the plurality of functional groups comprise a first functional group comprising a $C_6$-$C_{30}$ alkyl chain attached to the repeating unit through a carbonyl group (C═O) via an ester linkage, a second functional group comprising a partially fluorinated or perfluorinated $C_3$-$C_{20}$ alkyl chain attached to the repeating unit through a carbonyl group (C═O) via an ester linkage, and a third functional group comprising substantially one of (a) a stabilized radical source attached to the repeating unit via a $C_0$-$C_6$ tether, wherein the stabilized radical source is a 5 or 6 member heterocycle of carbon and nitrogen, which may be substituted with alkyl groups α (alpha) to the stabilized radical that sterically stabilizes the oxygen free radical, or (b) a 5 to 8 member chloroamide heterocycle of carbon and nitrogen that is attached to the repeating unit via a $C_2$-$C_6$ tether.

At least some embodiments of the present invention relate to a hyperbranched polymer that can advantageously be used to enhance microorganism growth atop a substrate, wherein the hyperbranched polymer is based on one or more repeating units of the following structure:

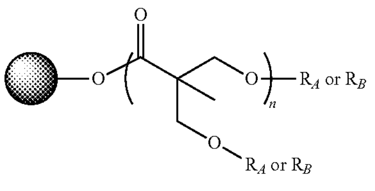

wherein one or more of $R_A$ and $R_B$ is one of a bond to another repeating unit or, represents the fractional functionalization of the hyperbranched polymer by a plurality of functional groups, wherein the plurality of functional groups comprise a first functional group comprising a $C_6$-$C_{30}$ alkyl chain attached to the repeating unit through a carbonyl group (C═O) via an ester linkage, a second functional group comprising a partially fluorinated or perfluorinated $C_3$-$C_{20}$ alkyl chain attached to the repeating unit through a carbonyl group (C═O) via an ester linkage, and a third functional group comprising substantially one of: (a) a stabilized radical source attached to the repeating unit via a $C_0$-$C_6$ tether, wherein the stabilized radical source is a 5 or 6 member heterocycle of carbon and nitrogen, which may be substituted with alkyl groups α (alpha) to the stabilized radical that sterically stabilizes the oxygen free radical, or (b) a 5 to 8 member chloroamide heterocycle of carbon and nitrogen that is attached to the repeating unit via a $C_2$-$C_6$ tether.

At least some embodiments of the present invention relate to a method of enhancing microorganism growth atop a substrate, comprising forming a hyperbranched polymer based on one or more repeating units of the following formula:

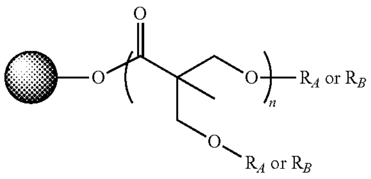

wherein one of either $R_A$ or $R_B$ is one of a bond to another repeating unit or represents the fractional functionalization of the hyperbranched polymer by a plurality of functional groups, wherein the plurality of functional groups comprises a first functional group comprising a $C_6$-$C_{30}$ alkyl chain attached to the repeating unit through a carbonyl group (C═O) via an ester linkage, a second functional group comprising a partially fluorinated or perfluorinated $C_3$-$C_{20}$ alkyl chain attached to the repeating unit through a carbonyl group (C═O) via an ester linkage, and a third functional group comprising substantially one of: (a) a stabilized radical source attached to the repeating unit via a $C_0$-$C_6$ tether, wherein the stabilized radical source is a 5 or 6 member heterocycle of carbon and nitrogen, which may be substituted with alkyl groups α (alpha) to the stabilized radical that sterically stabilizes the oxygen free radical, or (b) a 5 to 8 member chloroamide heterocycle of carbon and nitrogen that is attached to the repeating unit via a $C_2$-$C_6$ tether; mixing the hyperbranched polymer with a solution to form a first mixture; curing the first mixture to form a substrate, wherein the hyperbranched polymer spontaneously segregates to an air interface of the substrate; and introducing one or more microorganisms atop the surface of the substrate, wherein the hyperbranched polymer enhances microorganism growth at the air interface of the substrate.

Other and further embodiments of the invention are described in more detail below.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

Figure 1:
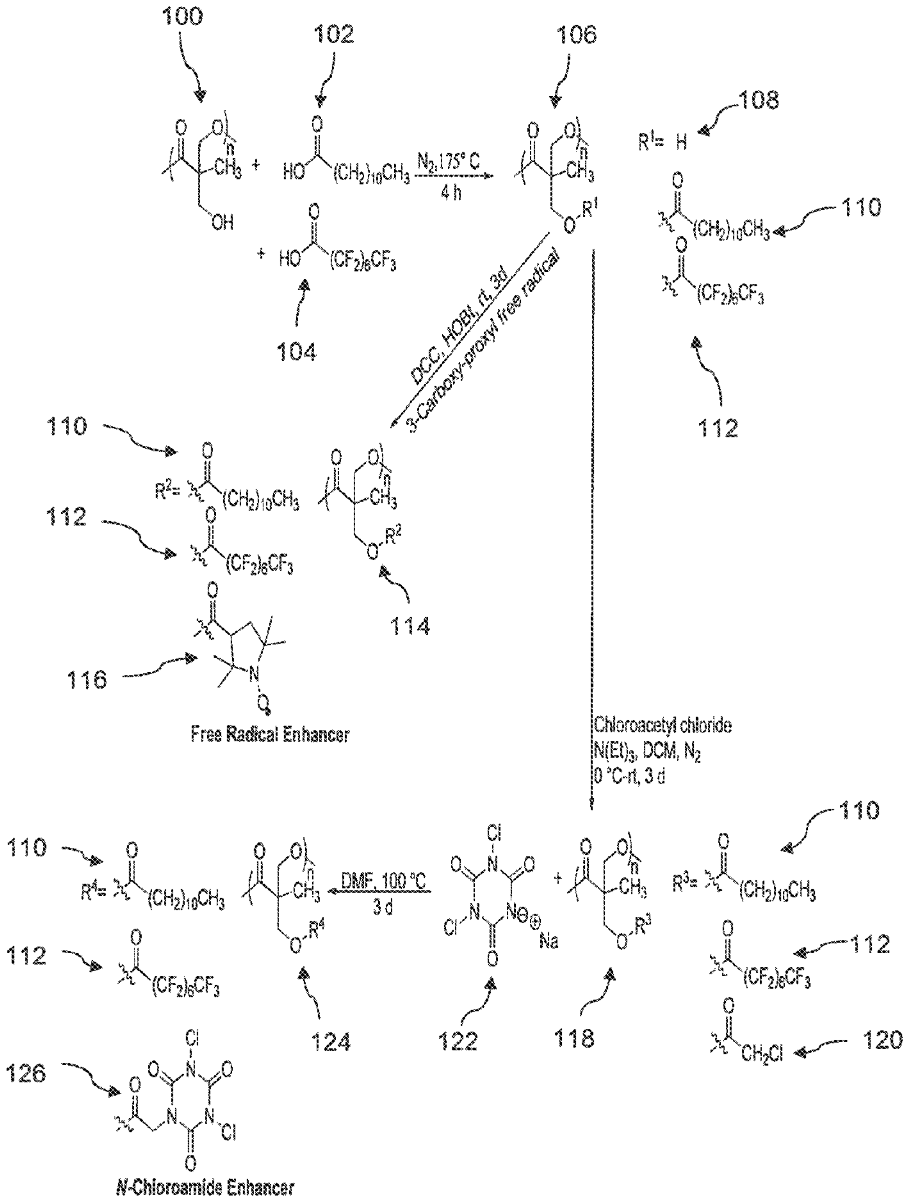
FIG. 1 depicts the synthesis of an exemplary hyperbranched polymer in accordance with some embodiments of the present invention.

To facilitate understanding, identical reference numerals have been used, where possible, to designate identical elements that are common to the figures. The figures are not drawn to scale and may be simplified for clarity. It is contemplated that elements and features of one embodiment may be beneficially incorporated in other embodiments without further recitation.

DETAILED DESCRIPTION

Embodiments of the present invention include additives that promote the growth of microorganisms. Additives in accordance with embodiments described herein advantageously promote the growth of microorganisms on a wide variety of surfaces, including surfaces that may be unsuitable for microorganism growth without the additive. Additives in accordance with embodiments described herein advantageously spontaneously migrate, to the upper surface (air interface) of a substrate to infuse the substrate with a high concentration of the additive at the air interface. Additives in accordance with embodiments described herein may advantageously be used in producing a substrate, thereby providing the substrate with inherent microorganism growth properties. Alternatively, additives in accordance with embodiments described herein may advantageously be incorporated into materials suitable for coating a substrate. Furthermore, additives in accordance with embodiments described herein advantageously provide an increase of about 10% to about 60% in the growth of Gram positive bacteria, Gram negative bacteria, and fungi.

Embodiments of the present invention relate to a hyperbranched polymer that can advantageously be used to modify a substrate to enhance microorganism growth atop the substrate. In some embodiments the hyperbranched polymer is based on one or more repeating units of an $AB_x$ type monomer. In some embodiments, A and B are functional groups and x is greater than or equal to 2. In some embodiments, the A functional group reacts with, or substantially reacts with, only the B functional group. In some embodiments, the A functional group can be one of, for example, an acid, an amine, a thiol, or a terminal alkyne. In some embodiments, the B functional group can be one of, for example, an alcohol, an acrylate or methacrylate (Michael addition partner), or a vinyl group, or an azide. It is appreciated that the class of reactive groups that comprise "click" chemistry partners would be especially suitable for this approach, whereby efficient and orthogonal (A+B) coupling pairs have been identified. Some examples were presented above (thiol-ene, alkyne-azide), but the list is illustrative only and is not exhaustive nor limiting.

In some embodiments, B is fractionally functionlized with a plurality of functional groups described below. One exemplary structure obtained from the polymerization of an $AB_x$ type monomer and its specific functionalization with a plurality of functional groups is as follows:

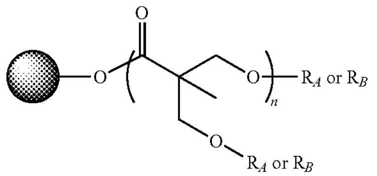

The structure above shows a repeat unit of the hyperbranched polymer with two functional groups, $R_A$ and $R_B$. The particle bonded to the repeat unit at the left represents either the focal point of a pseudo-dendron or a bond to a core molecule.

In some embodiments, one or more of $R_A$ and $R_B$ is one of a bond to another repeating unit or, represents the fractional functionalization of the hyperbranched polymer by a plurality of functional groups. The plurality of functional groups comprises a first functional group, a second functional group, and a third functional group described below, and modified onto the polymer chain end groups detailed herein.

In some embodiments, the first functional group is a $C_6$-$C_{30}$ alkyl chain attached to the repeating unit through a carbonyl group (C═O) via an ester linkage. For example, the first functional group may be an alkyl ester having the formula $(C{=}O)C_nH_{2n+1}$. In some embodiments, the first functional group is an aliphatic ester.

In some embodiments, the second functional group is a partially fluorinated or perfluorinated $C_3$-$C_{20}$ alkyl chain attached to the repeating unit through a carbonyl group (C═O). For example the second functional group may be an alkyl ester having the formula $(C{=}O)C_nF_{2n+1}$, or $(C{=}O)CH_2C_nF_{2n+1}$. It is recognized that other linkages may be employed to attach functional groups to the hyperbranched polymer core, dictated by the relative chemistries of both the polymer core and the desired functional group. Linkages in addition to the shown esters include but are not limited to ethers, urethanes, amines, amides, ureas, and siloxanes.

In some embodiments, the first functional group is lauric ester having the formula $-(C{=}O)(CH_2)_{10}CH_3$. The lauric ester group advantageously increases the solubility of the repeating unit above in most organic solvents. In some embodiments, the second functional goup is perfluorinated octyl-ester having the formula $-(C{=}O)(CF_2)_6CF_3$. The perfluorinated octyl-ester advantageously allows the repeating unit above to segregate to the surface of a substrate or film. In the most advantageous embodiment, $R_A$ is a mixture of both aliphatic ester and perfluorinated octyl-ester to maximize both solubility and propensity to surface segregate. The incorporation of the lauric ester group and the perfluorinated octyl-ester is described in U.S. Pat. No. 7,560,520, incorporated herein by reference.

In some embodiments the third functional group is a stabilized radical source. In some embodiments, the stabilized radical source is, for example (2,2,6,6-Tetramethyl-1-piperidinyloxy, free radical (TEMPO) or an N-proxyl radical. In some embodiments, the stabilized radical source can be attached to the repeating unit through a $C_0$-$C_6$ tether. In some embodiments, the stabilized radical source incorporates a 5 or 6 member heterocycle of carbon and nitrogen, which may be substituted with alkyl groups α (alpha) to the stabilized radical that sterically stabilizes the oxygen free radical. In embodiments where the hyperbranched polymer comprises substantially the stabilized radical source, the hyperbranched polymer is referred to herein as a free radical enhancer.

In some embodiments, the third functional group is a 3-(carboxy)-2,2,5,5-tetramethyl-1-pyrrolidinyloxy free radical (refered to as 3-carboxy-proxyl free radical) having the formula $C_9H_{15}NO_2$. The 3-carboxy-proxyl free radical advantageously promotes the growth of bacterial microorganisms, broadly including classes of organisms such as gram-positive, gram-negative, and fungal organisms. Specific examples include *E. coli, S. aureus*, MRSA, and *C. albicans*.

Alternatively, in some embodiments the third functional group is a 5 to 8 member chloroamide heterocycle of carbon and nitrogen that is attached to the repeating unit via a $C_2$-$C_6$ tether. In some embodiments, the third functional group is dichloro-s-triazinetrione (referred to as dichloroisocyanurate,) having the formula $C_3Cl_2N_3O_3$. It is recognized that this structure stabilizes oxidative chlorine species, but in this instance the dichloroisocyanurate advantageously leads to the growth of bacterial microorganisms such as *E. coli*, or, or *S. aureus*, or the like. In embodiments where the third functional group is a 5 to 8 member chloramide heterocycle attached to the repeating unit via a $C_2$-$C_6$ tether, the hyperbranched polymer is referred to herein as a N-chloroamide enhancer.

In some embodiments, the hyperbranched polymer comprises about 10 mole % to about 30 mole % of the lauric ester, about 10 mole % to about 25 mole % of the perfluorinated octyl-ester group, and about 50 mole % to about 75 mole % of the 3-carboxy-proxyl free radical. In some embodiments, the hyperbranched polymer comprises about 10 mole % to about 30 mole % of the lauric ester, about 10 mole % to about 25 mole % of the perfluorinated octyl-ester group, and about 50 mole % to about 75 mole % of the dichloroisocyanurate group.

FIG. 1 depicts an exemplary synthesis route for a hyperbranched polymer in accordance with some embodiments of the present invention. Other synthesis routes may be available to persons of ordinary skill in the art to produce the hyperbranched polymer structures depicted in FIG. 1. As depicted in FIG. 1, a first hyperbranched polymer 100 is mixed with lauric acid 102 and perfluorinated octanoic acid 104, resulting in a intermediate hyperbranched polymer 106. As depicted in FIG. 1, the chain ends, $R^1$, in the intermediate 106 comprise about 60 mole % hydrogen 108, about 20 mole % lauric ester 110, and about 20 mole % perfluorinated octyl-ester 112.

In order to synthesize the free radical enhancer, the intermediate 106 is mixed with dicyclohexylcarbodiimide (DCC) and hydroxy benzotriazole (HOBt) to form the hyperbranched polymer 114 having the one or more repeating units depicted above. As described above, the hyperbranched polymer 114 comprises chain ends, $R^2$, representing about 20 mole % lauric ester 110, about 20 mole % perfluorinated octyl-ester 112, and about 60 mole % 3 carboxy-proxyl free radical 116.

Alternatively, in order to synthesize the N-chloroamide enhancer intermediate 106, is reacted with chloroacetyl chloride, triethylamine, dichloromethane, and nitrogen (N2) to form intermediate 118. As depicted in FIG. 1, the chain ends, $R^3$, in intermediate 118 represent about 20 mole % lauric ester 110, about 20 mole % perfluorinated octyl-ester 112, and about 60 mole % chloromethylene 120. Intermediate 118 is then reacted with sodium dichloroisocyanurate 122 to form the hyperbranched polymer 124 having one or more repeating units as depicted above. As described above, the hyperbranched polymer 124 comprises chain ends, $R^4$, representing about 20 mole % lauric ester 110, about 20 mole % perfluorinated octyl-ester 112, and about 60 mole % dichloroisocyanurate 126.

Figure 2:
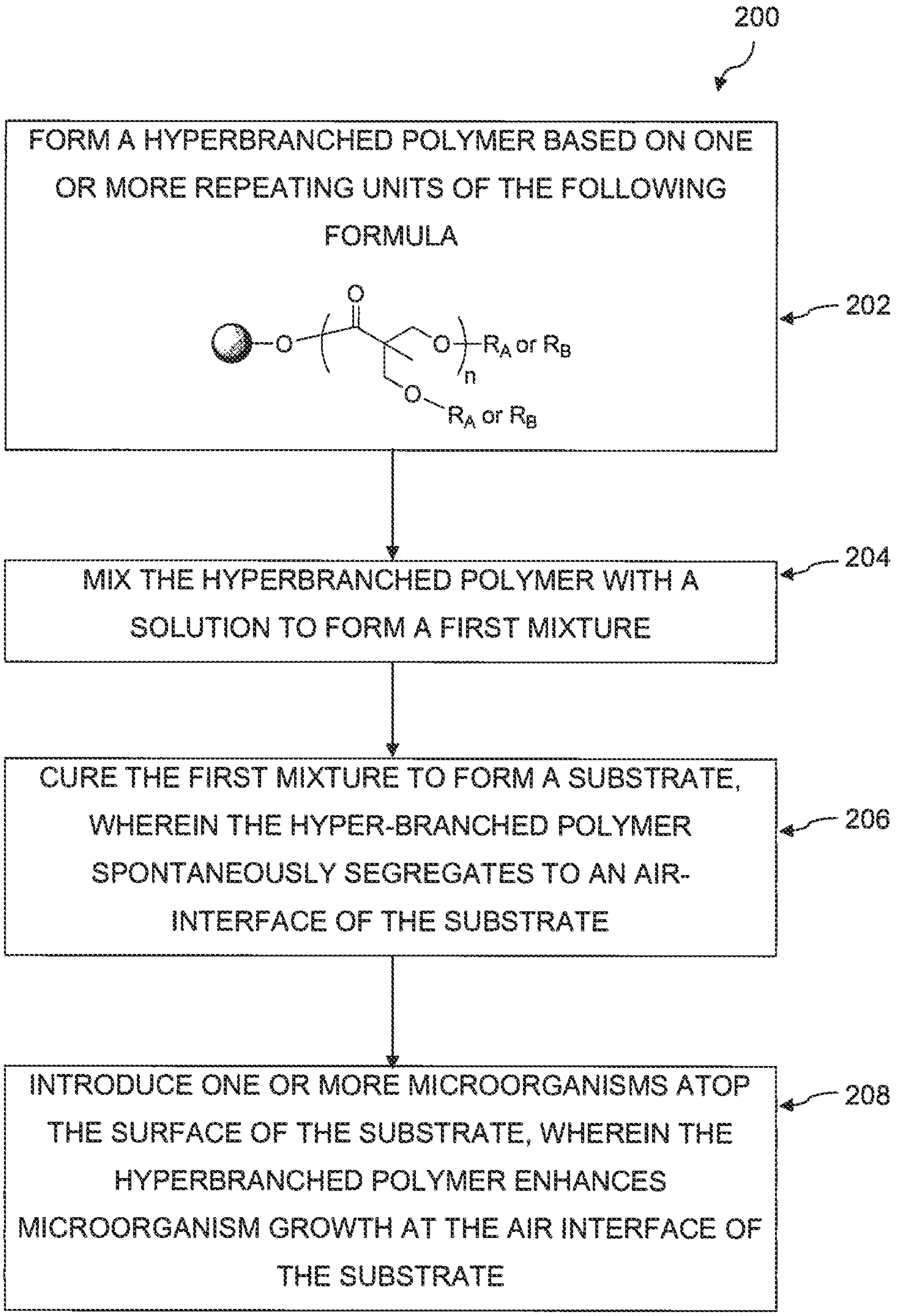
FIG. 2 depicts a method of enhancing the microorganism growth atop a substrate in accordance with some embodiments of the present invention.

FIG. 2 depicts a method of enhancing the bacterial growth atop a substrate in accordance with some embodiments of the present invention. In some embodiments, the method 200 of enhancing bacterial growth atop a substrate begins at 202 by forming the hyperbranched polymer, either the free radical enhancer or the N-chloroamide enhancer, as described above. Next, at 204, the hyperbranched polymer is mixed with a polymer solution to form a first mixture. In some embodiments, the polymer solution can be a wide variety of polymers including but not limited to polyurethane (e.g. estane), styrinics (e.g. polystyrene), acrylics (e.g. polymethylmethacrylate, latexes), engineering plastics (e.g. polycarbonate), epoxy, reactive urethane or the like. The polymer solution is dissolved in a solvent, such as tetrahydrofuran (THF), or methylene chloride, or ketone (e.g. acetone, methyl ethyl ketone), and including systems dispersed in water or fully aqueous soluble (e.g. in a water dispersible polyurethane substrate). Next, at 206, the first mixture is cured to allow the solvent to evaporate resulting in a polymer film comprising the hyperbranched polymer. As the solvent evaporates the presence of the perfluorinated octyl-ester group results in the segregation of the hyperbranched polymer to the surface of the polymer film. Next, at 208, one or more microorganisms are introduced atop the surface of the polymer film, wherein the hyperbranched polymer enhances microorganism growth at the surface of the polymer film. Alternatively, in some embodiments, the hyperbranched polymer may be mixed with a soluble material such as paint, polymer, or polymer precursors and applied to the surface of a substrate The inventors have observed that the hyperbranched polymer unexpectedly enhances the growth of bacterial microorganisms. While a typical additive with highly efficient antimicrobial function would reduce microbial growth by about 90% to about 99%, in the current instance, the hyperbranched polymer caused the improved growth of all organisms deposited on the substrate surface. For example, the impact on growth rates for Gram (+), Gram (−), and *C. albicans* organisms of about 2% additive in a thermoplastic polyurethane film is shown below in Table 1.

Growth Additive

| Organism | Organism Type | Gram Indicator | Average CFU Increase: N-Chloramide | Average CFU Increase: Free Radical |
|---|---|---|---|---|
| *Staphylococcus aureus* | Bacteria | + | 53 | 60 |
| Methicillin-resistant *Staphylococcus aureus* | Bacteria | + | 18 | Not tested |
| *Escherichia coli* | Bacteria | − | 61 | 630 |
| *Candida albicans* | Fungi | n/a | 34 | Not tested |

*as compared with inoculated controls (1 × $10^6$ Colony Forming Units (CFU)/sample)

While the foregoing is directed to embodiments of the present invention, other and further embodiments of the invention may be devised without departing from the basic scope thereof.

The invention claimed is:

1. A hyperbranched polymer used to enhance bacterial growth atop a substrate, wherein the hyperbranched polymer contains one or more repeating units of the following structure:

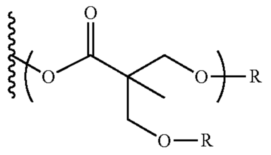

wherein each R individually represents either $R_A$ or $R_B$; wherein $R_A$ is a bond to another repeating unit and $R_B$ represents the fractional functionalization of the hyperbranched polymer by a plurality of functional groups, wherein the plurality of functional groups comprise:

a first functional group comprising a $C_6$-$C_{30}$ alkyl chain attached to the repeating unit through a carbonyl group (C═O) via an ester linkage, a second functional group comprising a partially fluorinated or perfluorinated $C_6$-$C_{20}$ alkyl chain attached to the repeating unit through a carbonyl group (C═O) via an ester linkage, and a third functional group comprising substantially one of: (a) a stabilized radical source attached to the repeating unit via a $C_0$-$C_{20}$ tether, wherein the stabilized radical source is a 5 or 6 member heterocycle of carbon and nitrogen, which may be substituted with alkyl groups α(alpha) to the stabilized radical that sterically stabilizes an oxygen free radical, or (b) a 5 to 8 member chloroamide heterocycle of carbon and nitrogen that is attached to the repeating unit via a $C_2$-$C_6$ tether;

and wherein $R_A$ and $R_B$ are each resent in the hyperbranched polymer.

2. The hyperbranched polymer of claim 1, wherein the first functional group is a lauric ester.

3. The hyperbranched polymer of claim 2, wherein the second functional group is a perfluorinated octyl-ester.

4. The hyperbranched polymer of claim 3, wherein the third functional group is substantially one of a 3-(carboxy)-2,2,5,5-tetramethyl-1-pyrrolidinyloxy free radical or a dichloro-s-triazinetrione.

5. The hyperbranched polymer of claim 4, further comprising about 10 mole % to about 30 mole % of the lauric ester, about 10 mole % to about 25 mole % of the perfluorinated octyl-ester, and about 50 mole % to about 75mole % of the 3-(carboxy)-2,2,5,5-tetramethyl-1-pyrrolidinyloxy free radical.

6. The hyperbranched polymer of claim 4, further comprising about 10 mole % to about 30 mole % of the lauric ester, about 10 mole % to about 25 mole % of the perfluorinated octyl-ester group, and about 50 mole % to about 75 mole % of the dichloro-s-triazinetrione.

* * * * *